(12) United States Patent
Leir et al.

(10) Patent No.: US 7,652,163 B2
(45) Date of Patent: *Jan. 26, 2010

(54) CYCLIC SILAZANES CONTAINING AN OXAMIDO ESTER GROUP AND METHODS

(75) Inventors: Charles M. Leir, Falcon Heights, MN (US); Karl E. Benson, St. Paul, MN (US); Richard G. Hansen, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/368,757

(22) Filed: Feb. 10, 2009

(65) Prior Publication Data

US 2009/0143557 A1 Jun. 4, 2009

Related U.S. Application Data

(62) Division of application No. 11/821,571, filed on Jun. 22, 2007, now Pat. No. 7,507,849.

(51) Int. Cl.
*C07F 7/00* (2006.01)
(52) U.S. Cl. .................. 556/466; 528/10; 528/33; 528/34; 528/38; 556/407; 556/410; 556/411; 556/413; 556/425; 556/450; 556/467
(58) Field of Classification Search .................. 528/10, 528/33–34, 38; 556/413, 425, 450, 407, 556/410, 411, 466, 467
See application file for complete search history.

(56) References Cited

U.S. PATENT DOCUMENTS

| | | | |
|---|---|---|---|
| 2,532,011 A | 11/1950 | Dahlquist | |
| 2,676,182 A | 4/1954 | Daudt | |
| 2,736,721 A | 2/1956 | Dexter | |
| 3,627,861 A | 12/1971 | Brady | |
| 3,772,247 A | 11/1973 | Flannigan | |
| 3,890,269 A | 6/1975 | Martin | |
| 4,119,615 A | 10/1978 | Schulze | |
| 4,661,577 A | 4/1987 | Jo Lane | |
| 4,889,753 A | 12/1989 | Brown | |
| 4,935,484 A | 6/1990 | Wolfgruber | |
| 4,981,988 A | 1/1991 | Ichinohe | |
| 5,026,890 A | 6/1991 | Webb | |
| 5,082,706 A | 1/1992 | Tangney | |
| 5,091,483 A | 2/1992 | Mazurek | |
| 5,110,890 A | 5/1992 | Butler | |
| 5,214,119 A | 5/1993 | Leihr | |
| 5,248,739 A | 9/1993 | Schmidt | |
| 5,276,122 A | 1/1994 | Aoki | |
| 5,290,615 A | 3/1994 | Tushaus | |
| 5,302,685 A | 4/1994 | Tsumura | |
| 5,319,040 A | 6/1994 | Wengrovius | |
| 5,461,134 A | 10/1995 | Leir | |
| 5,512,650 A | 4/1996 | Leir | |
| 5,539,033 A | 7/1996 | Bredahl | |
| 5,663,262 A | 9/1997 | Shirakawa | |
| 5,981,680 A | 11/1999 | Petroff | |
| 6,051,216 A | 4/2000 | Barr | |
| 6,355,759 B1 | 3/2002 | Sherman | |
| 6,407,195 B2 | 6/2002 | Sherman | |
| 6,441,118 B2 | 8/2002 | Sherman | |
| 6,531,620 B2 | 3/2003 | Brader | |
| 6,534,615 B2 | 3/2003 | Schafer | |
| 6,664,359 B1 | 12/2003 | Kangas | |
| 6,730,397 B2 | 5/2004 | Melancon | |
| 6,846,893 B1 | 1/2005 | Sherman | |
| 7,026,424 B2 | 4/2006 | Schafer | |
| 7,153,924 B2 | 12/2006 | Kuepfer | |
| 2003/0165676 A1 | 9/2003 | Zhou | |
| 2003/0175510 A1 | 9/2003 | Sherman | |
| 2003/0235553 A1 | 12/2003 | Lu | |
| 2004/0115153 A1 | 6/2004 | Yu | |
| 2004/0120912 A1 | 6/2004 | Yu | |
| 2005/0136266 A1 | 6/2005 | Zhou | |
| 2006/0194937 A1 | 8/2006 | Schafer | |
| 2007/0148474 A1 | 6/2007 | Leir | |
| 2007/0148475 A1 | 6/2007 | Sherman | |
| 2007/0149745 A1 | 6/2007 | Leir | |
| 2007/0177272 A1 | 8/2007 | Benson | |
| 2007/0177273 A1 | 8/2007 | Benson | |

FOREIGN PATENT DOCUMENTS

| | | |
|---|---|---|
| DE | 4234846 | 4/1994 |
| EP | 0311262 A2 | 4/1989 |
| EP | 0311262 A3 | 4/1989 |
| EP | 0378420 A2 | 7/1990 |
| EP | 0378420 A3 | 7/1990 |
| EP | 0433070 A2 | 6/1991 |
| EP | 0433070 A3 | 6/1991 |
| EP | 0311262 | 12/1992 |
| EP | 0433070 | 1/1996 |
| JP | HEI-2-36234 | 2/1990 |

(Continued)

OTHER PUBLICATIONS

ASTM-D 1003-95, "Standard Test Method for Haze and Luminous Transmittance of Transparent Plastics," Annual Book of ASTM Standards, pp. 197-201 (1995).

(Continued)

*Primary Examiner*—Randy Gulakowski
*Assistant Examiner*—Olatunde S Ojurongbe
(74) *Attorney, Agent, or Firm*—Colene H. Blank

(57) ABSTRACT

Cyclic silazanes containing an oxamido ester group and methods of making these compounds are described. The compounds can be used, for example, to make oxamido ester-terminated siloxanes, which can be precursors for the preparation of various polymeric materials such as, for example, polydiorganosiloxane polyoxamides.

15 Claims, No Drawings

FOREIGN PATENT DOCUMENTS

| | | |
|---|---|---|
| JP | 2002-020392 | 1/2002 |
| JP | 2002/036234 | 2/2002 |
| WO | WO 97/40103 | 10/1997 |
| WO | WO 2004/054523 | 7/2004 |

OTHER PUBLICATIONS

Encyclopedia of Polymer Science and Engineering, vol. 15, John Wiley & Sons, New York, (1989), pp. 265-270).

McGrath, et al, "Synthesis and Characterization of Segmented Siloxane Copolymers." Polymer Preprints, vol. 39, No. 1, Mar. 1998, pp. 455-456.

Nielsen, et al. Viscoelastic Damper Overview for Seismic and Wind Applications, Proceedings of SPIE—vol. 2720, Smart Structures and Materials 1996, Passive Damping and Isolation, Conor D. Johnson, Editor, May 1996, pp. 138-144.

U.S. Appl. No. 11/821,568, filed Jun. 22, 2007.
U.S. Appl. No. 11/821,572, filed Jun. 22, 2007.
U.S. Appl. No. 11/821,575, filed Jun. 22, 2007.
U.S. Appl. No. 11/821,596, filed Jun. 22, 2007.

CYCLIC SILAZANES CONTAINING AN OXAMIDO ESTER GROUP AND METHODS

CROSS REFERENCE TO RELATED APPLICATIONS

This application is a divisional of U.S. Ser. No. 11/821,571, filed Jun. 22, 2007 now U.S. Pat. No. 7,507,849, now allowed, the disclosure of which is incorporated by referenced in its entirety herein.

TECHNICAL FIELD

Cyclic silazanes containing an oxamido ester group and methods of making and using these compounds are described.

BACKGROUND

Siloxane polymers have unique properties derived mainly from the physical and chemical characteristics of the siloxane bond. These properties include low glass transition temperature, thermal and oxidative stability, resistance to ultraviolet radiation, low surface energy and hydrophobicity, high permeability to many gases, and biocompatibility. The siloxane polymers, however, often lack tensile strength.

The low tensile strength of the siloxane polymers can be improved by forming block copolymers. Some block copolymers contain a "soft" siloxane polymeric block or segment and any of a variety of "hard" blocks or segments. Exemplary block copolymers include polydiorganosiloxane polyamides and polydiorganosiloxane polyureas.

Polydiorganosiloxane polyamides have been prepared by condensation reactions of amino terminated silicones with short-chained dicarboxylic acids. Alternatively, these copolymers have been prepared by condensation reactions of carboxy terminated silicones with short-chained diamines. Because polydiorganosiloxanes (e.g., polydimethylsiloxanes) and polyamides often have significantly different solubility parameters, it can be difficult to find reaction conditions for production of siloxane-based polyamides that result in high degrees of polymerization, particularly with larger homologs of the polydiorganosiloxane segments. Many of the known siloxane-based polyamide copolymers contain relatively short segments of the polydiorganosiloxane (e.g., polydimethylsiloxane) such as segments having no greater than 30 diorganosiloxy (e.g., dimethylsiloxy) units or the amount of the polydiorganosiloxane segment in the copolymer is relatively low. That is, the fraction (i.e., amount based on weight) of polydiorganosiloxane soft segments in the resulting copolymers tends to be low.

SUMMARY

Cyclic silazanes containing an oxamido ester group and methods of making these compounds are described. The compounds can be used, for example, to make oxamido ester-terminated siloxanes, which can be precursors for the preparation of various polymeric materials such as, for example, polydiorganosiloxane polyoxamides.

In one aspect, the present disclosure provides a compound of Formula I:

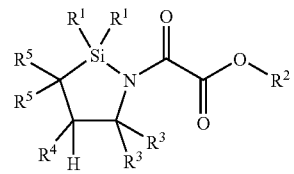

I wherein: each $R^1$ is independently an alkyl, haloalkyl, aralkyl, alkenyl, aryl, or aryl substituted with an alkyl, alkoxy, or halo; $R^2$ is an alkyl, haloalkyl, aryl, or aryl substituted with an alkyl, alkoxy, halo, or alkoxycarbonyl; and each $R^3$, $R^4$, and $R^5$ is independently hydrogen or an alkyl, haloalkyl, aralkyl, alkenyl, aryl, or aryl substituted with an alkyl, alkoxy, or halo. Methods of making a compound of Formula I are also disclosed herein.

In another aspect, the present disclosure also provides a method of making a polymer precursor of Formula III:

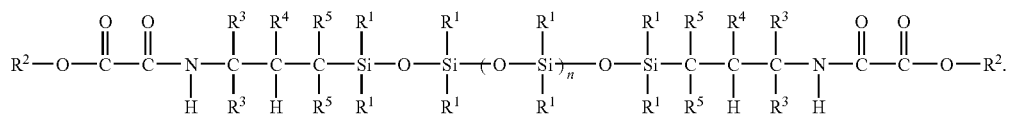

III

The method includes combining under reaction conditions: a compound of Formula I as described above and a silanol terminated siloxane of Formula II:

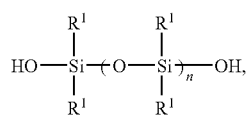

II wherein: each $R^1$ is independently an alkyl, haloalkyl, aralkyl, alkenyl, aryl, or aryl substituted with an alkyl, alkoxy, or halo; and n is an integer of 0 to 1500.

In still another aspect, the present disclosure provides a method of making a polymeric material including at least two repeat units of Formula VIII:

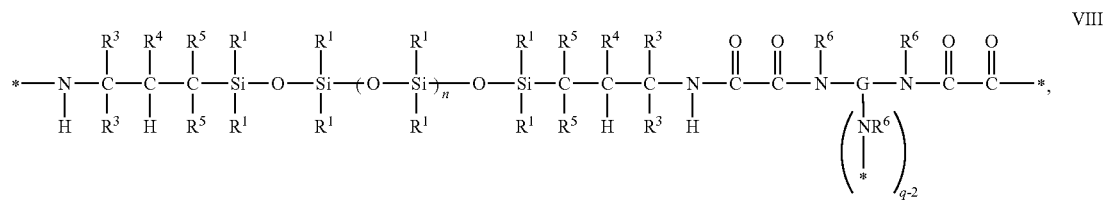

wherein q is an integer greater than or equal to 2. The method includes (i) combining under reaction conditions: a compound of Formula I as described above and a silanol terminated siloxane of Formula II:

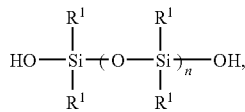

to form a polymer precursor of Formula III:

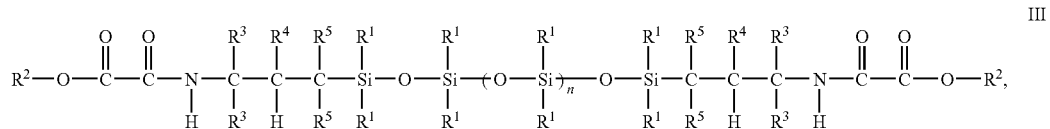

wherein: each $R^1$ is independently an alkyl, haloalkyl, aralkyl, alkenyl, aryl, or aryl substituted with an alkyl, alkoxy, or halo; $R^2$ is an alkyl, haloalkyl, aryl, or aryl substituted with an alkyl, alkoxy, halo, or alkoxycarbonyl; each $R^3$, $R^4$, and $R^5$ is independently hydrogen or an alkyl, haloalkyl, aralkyl, alkenyl, aryl, or aryl substituted with an alkyl, alkoxy, or halo; and n is an integer of 0 to 1500; and (ii) combining under reaction conditions the formed polymer precursor of Formula III with one or more amine compounds having on average a formula $G(NHR^6)_r$; wherein: G is a residue unit equal to the formula $G(NHR^6)_r$ minus the r —$NHR^6$ groups; $R^6$ is hydrogen or alkyl (e.g., an alkyl having 1 to 10, 1 to 6, or 1 to 4 carbon atoms) or $R^6$ taken together with G and with the nitrogen to which they are both attached forms a heterocyclic group; and r is a number greater than or equal to 2.

The presently disclosed polymeric materials can be conceived for use in numerous applications including, for example, in sealants, adhesives, as material for fibers, as plastics additives, e.g., as impact modifiers or flame retardants, as material for defoamer formulations, as a high-performance polymer (thermoplastic, thermoplastic elastomer, elastomer), as packaging material for electronic components, in insulating materials or shielding materials, in cable sheathing, in antifouling materials, as an additive for scouring, cleaning, or polishing products, as an additive for body care compositions, as a coating material for wood, paper, and board, as a mold release agent, as a biocompatible material in medical applications such as contact lenses, as a coating material for textile fibers or textile fabric, as a coating material for natural substances such as leather and furs, for example, as a material for membranes and as a material for photoactive systems, for example, for lithographic techniques, optical data securement or optical data transmission.

DEFINITIONS

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "a", "an", and "the" are used interchangeably with "at least one" to mean one or more of the elements being described.

As used herein, the term "or" is generally employed in its sense including "and/or" unless the content clearly dictates otherwise.

The term "and/or" means one or all of the listed elements or a combination of any two or more of the listed elements.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where R is an alkyl group and (CO) denotes a carbonyl group with the carbon attached to the oxygen with a double bond.

The term "aralkyl" refers to a monovalent group of formula —$R^3$—Ar where $R^a$ is an alkylene and Ar is an aryl group. That is, the aralkyl is an alkyl substituted with an aryl.

The term "aralkylene" refers to a divalent group of formula —$R^a$—$Ar^a$— where $R^a$ is an alkylene and $Ar^a$ is an arylene (i.e., an alkylene is bonded to an arylene).

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aryloxy" refers to a monovalent group of formula —OAr where Ar is an aryl group.

The term "carbonyl" refers to a divalent group of formula —(CO)— where the carbon atom is attached to the oxygen atom with a double bond.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "heteroalkylene" refers to a divalent group that includes at least two alkylene groups connected by a thio, oxy, or —NR— where R is alkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms. Some heteroalkylenes are polyalkylene oxides where the heteroatom is oxygen.

The term "oxalyl" refers to a divalent group of formula —(CO)—(CO)— where each (CO) denotes a carbonyl group.

The terms "oxalylamino" and "aminoxalyl" are used interchangeably to refer to a divalent group of formula —(CO)—(CO)—NH— where each (CO) denotes a carbonyl.

The term "aminoxalylamino" refers to a divalent group of formula —NH—(CO)—(CO)—$NR^d$— where each (CO) denotes a carbonyl group and $R^d$ is hydrogen, alkyl, or part of a heterocyclic group along with the nitrogen to which they are both attached. In most embodiments, $R^d$ is hydrogen or alkyl. In many embodiments, $R^d$ is hydrogen.

The term "polyvalent" refers to a group having a valence of greater than 2.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The term "polydiorganosiloxane" refers to a divalent segment of formula

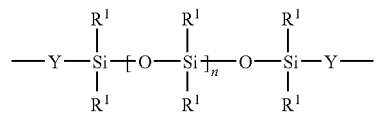

where each $R^1$ is independently an alkyl, haloalkyl, aralkyl, alkenyl, aryl, or aryl substituted with an alkyl, alkoxy, or halo; each Y is independently an alkylene, aralkylene, or a combination thereof, and subscript n is independently an integer of 0 to 1500.

The terms "room temperature" and "ambient temperature" are used interchangeably to mean temperatures in the range of 20° C. to 25° C.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION OF ILLUSTRATIVE EMBODIMENTS

Cyclic silazanes containing an oxamido ester group and methods of making these compounds are provided. The cyclic silazane compounds undergo ring opening reactions with hydroxy-functional molecules such as silanol terminated siloxanes. Thus, the cyclic silazanes can be used, for example, to make oxamido ester-terminated siloxanes, which can be used as precursors for the preparation of various polymeric materials such as, for example, polydiorganosiloxane polyoxamides, which can be used to form a wide variety of compositions and articles. See, for example, copending applications with Ser. No. 11/821,572 entitled "BRANCHED POLYDIORGANOSILOXANE POLYAMIDE COPOLYMERS;" Ser. No. 11/821,575 entitled "POLYDIORGANOSILOXANE POLYAMIDE COPOLYMERS HAVING ORGANIC SOFT SEGMENTS;" Ser. No. 11/865,841 entitled "MIXTURES OF POLYDIORGANOSILOXANE POLYAMIDE-CONTAINING COMPONENTS AND ORGANIC POLYMERS;" and Ser. No. 11/821,596 entitled "POLYDIORGANOSILOXANE POLYOXAMIDE COPOLYMERS", all filed on the same day herewith.

Cyclic Silazanes and Methods of Making Same

A cyclic silazane of Formula I is provided:

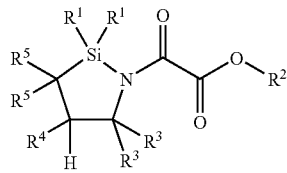

In this formula, each $R^1$ is independently an alkyl, haloalkyl, aralkyl, alkenyl, aryl, or aryl substituted with an alkyl, alkoxy, or halo. Each $R^2$ is independently an alkyl, haloalkyl, aryl, or aryl substituted with an alkyl, alkoxy, halo, or alkoxycarbonyl. Each $R^3$, $R^4$, and $R^5$ is independently hydrogen or an alkyl, haloalkyl, aralkyl, alkenyl, aryl, or aryl substituted with an alkyl, alkoxy, or halo.

Suitable alkyl groups for $R^1$, $R^3$, $R^4$, and/or $R^5$ typically have 1 to 10 carbon atoms, 1 to 6 carbon atoms, or 1 to 4 carbon atoms. Exemplary alkyl groups include, but are not limited to, methyl, ethyl, isopropyl, n-propyl, n-butyl, and iso-butyl. Suitable haloalkyl groups for $R^1$, $R^3$, $R^4$, and/or $R^5$ often have 3 to 10 carbon atoms and only a portion of the hydrogen atoms are replaced with a halogen. Exemplary haloalkyl groups include chloroalkyl and fluoroalkyl groups with 1 to 3 halo atoms and 3 to 10 carbon atoms. Suitable alkenyl groups for $R^1$, $R^3$, $R^4$, and/or $R^5$ often have 2 to 10 carbon atoms. Exemplary alkenyl groups often have 2 to 10, 2 to 6, or 2 to 4 carbon atoms such as ethenyl, n-propenyl, and n-butenyl. Suitable aryl groups for $R^1$, $R^3$, $R^4$, and/or $R^5$ often have 6 to 12 carbon atoms. Phenyl is an exemplary aryl group. An aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy with 1 to 10 carbon atoms, 1 to 6 carbon atoms, or 1 to 4 carbon atoms), or halo (e.g., chloro, bromo, or fluoro). Suitable aralkyl groups for $R^1$, $R^3$, $R^4$, and/or $R^5$ usually have an alkylene group having 1 to 10 carbon atoms and an aryl group with 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl with phenyl bonded to an alkylene).

In some compounds of Formula I, at least one, and preferably both $R^1$ groups are methyl. In some compounds of Formula I, at least one of $R^3$, $R^4$, and $R^5$ are hydrogen, and preferably each of $R^3$, $R^4$, and $R^5$ are hydrogen.

Suitable alkyl and haloalkyl groups for $R^2$ often have 1 to 10, 1 to 6, or 1 to 4 carbon atoms. Although tertiary alkyl (e.g., tert-butyl) and tertiary haloalkyl groups can be used, a primary or secondary carbon atom is often attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or fluoroalkyl groups can be chloromethyl, 2-chloroethyl, 2,2,2-trichloroethyl, 3-chloropropyl, 4-chlorobutyl, fluoromethyl, 2-fluoroethyl, 2,2,2-trifluoroethyl, 3-fluoropropyl, 4-fluorobutyl, and the like.

Suitable aryl groups for $R^2$ include those having 6 to 12 carbon atoms such as, for example, phenyl. An aryl group can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), or alkoxycarbonyl (e.g., an alkoxycarbonyl having 2 to 5 carbon atoms such as methoxycarbonyl, ethoxycarbonyl, or propoxycarbonyl).

Exemplary compounds according to Formula I include, but are not limited to, those in which $R^1$ is methyl and in which $R^3$, $R^4$, and $R^5$ are the same (e.g., hydrogen). $R^2$ can be an alkyl having 1 to 4 carbon atoms, haloalkyl having 1 to 4 carbon atoms, phenyl, phenyl substituted with an alkoxycarbonyl having 2 to 5 carbon atoms, phenyl substituted with at least one halo group, or phenyl substituted with an alkoxy having 1 to 4 carbon atoms. In certain embodiments $R^2$ is ethyl.

Cyclic silazanes of Formula I can conveniently be made, for example, by cyclization of a compound of Formula VII:

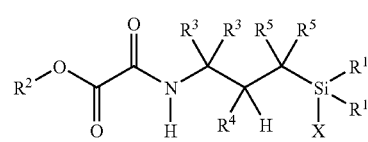

wherein: each $R^1$, $R^2$, $R^3$, $R^4$, and $R^5$ are as defined herein above for the compound of Formula I. X represents a halogen, and preferably is Cl.

In some embodiments, the cyclization occurs in the presence of a base, preferably an organic base. Typically, a compound of Formula VII can be dissolved in an appropriate organic solvent, and a soluble organic base can be added to result in the cyclization. A wide variety of organic solvents can be used. Exemplary organic solvents include, but are not limited to, tetrahydrofuran (THF), toluene, ethyl acetate, dichloromethane, and combinations thereof.

A wide variety of organic bases can be used. Exemplary organic bases include, but are not limited to, triethylamine (TEA), pyridine, N,N-dimethylaniline, N-methylimidazole, and combinations thereof.

Compounds of Formula VII can be conveniently made, for example, by hydrosilylation reactions. For example, a compound of Formula VII can be made by reacting a compound of Formula VI:

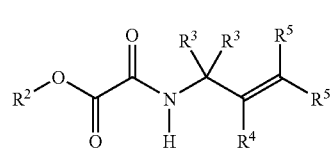

with a hydrosilane of the formula $(R^1)_2ClSiH$ in the presence of a hydrosilylation catalyst, wherein: each $R^1$, $R^2$, $R^3$, $R^4$, and $R^5$ are as defined herein above for the compound of Formula I. In certain embodiments reaction conditions include combining the compound of Formula VI with the hydrosilane of the formula $(R^1)_2ClSiH$ in a non-hydroxylic organic solvent in the presence of a platinum catalyst.

A wide variety of organic solvents can be used. Exemplary organic solvents include, but are not limited to, toluene, tetrahydrofuran (THF), ethyl acetate, dichloromethane, and combinations thereof.

Typical platinum hydrosilylation catalysts include, for example, chloroplatinic acid and the bis(divinyltetramethyldisiloxane)platinum complex known as the Carswell catalyst. The reaction is preferably conducted with excess hydrosilane (e.g., a 10-25% molar excess of the hydrosilane) using 0.05-1% by weight of Pt catalyst based on the total weight of the compound of Formula VI and the hydrosilane. In some embodiments, the reaction can be conducted at ambient temperature and pressure. In some other embodiments, the reaction can be conducted at 50° C. to 100° C. at elevated pressures in a pressure vessel.

Compounds of Formula VI can conveniently be made by combining an oxalate ester of Formula IV:

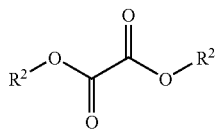

IV and an allylamine of Formula V:

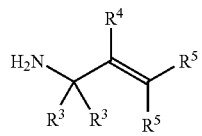

V under conditions effective to form the oxalamic acid ester. In certain embodiments, effective reaction conditions include combining excess oxalate ester of Formula IV (e.g., a 1 to 5 fold molar excess of the oxalate ester of Formula IV) and the allylamine of Formula V either neat or in an organic solvent. In some embodiments, the reaction can be conducted at ambient temperature and pressure. In some other embodiments, the reaction can be conducted at elevated temperatures, and optionally at elevated pressures in a pressure vessel. For embodiments in which an organic solvent is used, a wide variety of organic solvents can be used. Exemplary organic solvents include, but are not limited to, diethylether, tetrahydrofuran (THF), toluene ethanol, ethyl acetate, dichloromethane, and combinations thereof.

Reaction of Cyclic Silazanes of Formula I with Silanol Terminated Siloxanes

Cyclic silazanes of Formula I can be reacted with a silanol terminated siloxane of Formula II:

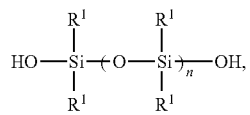

II to give a polymer precursor of Formula III:

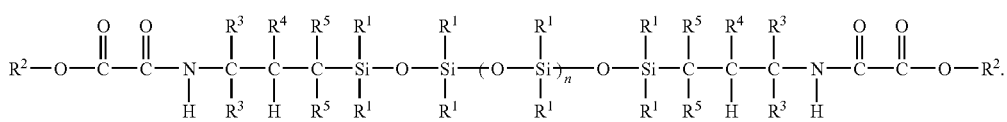

III

In silanol terminated siloxanes of Formula II, each $R^1$ is independently an alkyl, haloalkyl, aralkyl, alkenyl, aryl, or aryl substituted with an alkyl, alkoxy, or halo; and n is an integer of 0 to 1500.

In some compounds of Formula II, all $R^1$ groups can be one of alkyl, haloalkyl, aralkyl, alkenyl, aryl, or aryl substituted with an alkyl, alkoxy, or halo (e.g., all $R^1$ Groups are an alkyl such as methyl or an aryl such as phenyl). In some compounds of Formula II, the $R^1$ groups are mixtures of two or more selected from the group consisting of alkyl, haloalkyl, aralkyl, alkenyl, aryl, and aryl substituted with an alkyl, alkoxy, or halo in any ratio. Thus, for example, in certain compounds of Formula I, 0%, 1%, 2, %, 5%, 10%, 20%, 30%, 40%, 50%, 60%, 70%, 80%, 90%, 95%, 98%, 99%, or 100% of the $R^1$ groups can be methyl; and 100%, 99%, 98%, 95%, 90%, 80%, 70%, 60%, 50%, 40%, 30%, 20%, 10%, 5%, 2%, 1%, or 0% of the $R^1$ groups can be phenyl.

Each subscript n in Formulas II and III is independently an integer of 0 to 1500. For example, subscript n can be an integer up to 1000, up to 500, up to 400, up to 300, up to 200, up to 100, up to 80, up to 60, up to 40, up to 20, or up to 10. The value of n is often at least 1, at least 2, at least 3, at least 5, at least 10, at least 20, or at least 40. For example, subscript n can be in the range of 40 to 1500, 0 to 1000, 40 to 1000, 0 to 500, 1 to 500, 40 to 500, 1 to 400, 1 to 300, 1 to 200, 1 to 100, 1 to 80, 1 to 40, or 1 to 20.

Polymer precursors of Formula III can be prepared by combining a silanol terminated siloxane of Formula II with an amount of cyclic silazane of Formula I that is greater than or equal to the molar equivalents of silanol groups. The reaction can be conducted either neat or in a suitable organic solvent at a temperature of 25 to 100° C. Suitable solvents include, but are not limited to, tetrahydrofuran (THF), toluene, ethyl acetate, methylene chloride, and combinations thereof.

The polymer precursors of Formula III have groups of formula $R^2$—O—(CO)—(CO)—NH— at each end of the molecule. That is, the compounds have at least two oxalylamino groups. Each $R^2$ is independently an alkyl, haloalkyl, aryl, or aryl substituted with an alkyl, alkoxy, halo, or alkoxycarbonyl. The group of formula $R^2$O—(CO)—(CO)—NH— is an alkoxyoxalylamino group when $R^2$ is an alkyl, a haloalkoxyoxalylamino group when $R^2$ is a haloalkyl, or an aryloxyoxalylamino group when $R^2$ is an unsubstituted or substituted aryl.

The compounds of Formula III can be used as precursors for the preparation of various polymeric materials (e.g., elastomeric materials) including, for example, those described in U.S. patent application Ser. No. 11/317,271, filed 23 Dec. 2005. These polymeric materials can be used in various compositions including, for example, adhesive compositions as described in U.S. patent application Ser. No. 11/317,602, filed 23 Dec. 2005. These polymeric materials can be used in various articles including, for example, films and multilayer films as described in U.S. patent application Ser. Nos. 11/614,357 and 11/614,169, both filed 21 Dec. 2006.

The compounds of Formula III, either alone or optionally in combination with other precursor materials (e.g., other precursor materials having oxamido ester-terminated segments such as those including amide end-capped (e.g., oxalated) organic soft segments), can be reacted with one or more amine compounds to form linear and/or branched polymers.

For example, the compounds can undergo a condensation reaction when combined with one or more amine compounds having on average a formula $G(NHR^6)_r$; wherein: G is a residue unit equal to the formula $G(NHR^6)_r$ minus the r —$NHR^6$ groups; and r is a number greater than or equal to 2, to give a polymeric material having at least two repeat units of Formula VIII:

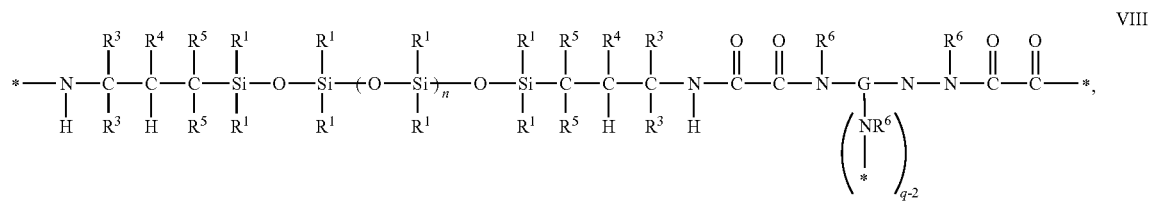

wherein q is an integer greater than or equal to 2. In certain embodiments q can, for example, be equal to 2, 3, or 4. The one or more amine compounds are typically on average of the formula $G(NHR^6)_r$ where r is a number greater than or equal to 2. Group $R^6$ is hydrogen or alkyl (e.g., an alkyl having 1 to 10, 1 to 6, or 1 to 4 carbon atoms) or $R^6$ taken together with G and with the nitrogen to which they are both attached forms a heterocyclic group (e.g., $R^6HN$-G-$NHR^6$ is piperazine). In most embodiments, $R^6$ is hydrogen or an alkyl. In many embodiments, all of the amino groups of the one or more amine compounds are primary amino groups (i.e., all the $R^6$ groups are hydrogen) and the one or more amine compounds are of the formula $G(NH_2)_q$ (e.g., a diamine of the formula $R^6HN$-G-$NHR^6$ when q=2). The $R^2OH$ by-product is typically removed from the resulting polydiorganosiloxane polyamide.

In certain embodiments, the one or more amine compounds are a mixture of (i) a diamine compound of formula $R^6HN$-G-$NHR^6$ and (ii) a polyamine compound of formula $G(NHR^6)_q$, where q is an integer greater than 2. In such embodiments, the polyamine compound of formula $G(NHR^6)_q$ can be, but is not limited to, triamine compounds (i.e., q=3), tetraamine compounds (i.e., q=4), and combinations thereof. In such embodiments, the number of equivalents of polyamine (ii) per equivalent of diamine (i) is preferably at least 0.001, more preferably at least 0.005, and most preferably at least 0.01. In such embodiments, the number of equivalents of polyamine (ii) per equivalent of diamine (i) is preferably at most 3, more preferably at most 2, and most preferably at most 1.

Exemplary triamines include, but are not limited to, tris(2-aminoethyl)amine, diethylentriamine, polyoxyalkylene triamines such as those available, for example, from Huntsman (The Woodlands, Tex.) under the trade designations JEFFAMINE T-3000 (i.e., polyoxypropropylene triamine having an average molecular weight of 3000 g/mole) and JEFFAMINE T-5000 (i.e., polyoxypropylene triamine having an average molecular weight of 5000 g/mole), amino-functional polysiloxanes, and combinations thereof. Exemplary tetraamines include, but are not limited to, triethylene tetraamine. Exemplary polydimethylsiloxanes having amino functionality include, for example, polydimethylsiloxane copolymers having aminopropylmethylsiloxane units such as those available under the trade designations AMS-132, AMS-152, and AMS-162 from Gelest, Inc., Morrisville, Pa.

When the one or more amine compounds include diamines, the diamines are sometimes classified as organic diamines or polydiorganosiloxane diamines with the organic diamines including, for example, those selected from alkylene diamines, heteroalkylene diamines, arylene diamines, aralkylene diamines, or alkylene-aralkylene diamines. Tertiary amines that do not react with the precursor of Formula II (II-a or II-b) can be present. Additionally, the diamine is free of any carbonylamino group. That is, the diamine is not an amide.

Exemplary polyoxyalkylene diamines (i.e., G is a heteroalkylene with the heteroatom being oxygen) include, but are not limited to, those commercially available from Huntsman, The Woodlands, Tex. under the trade designation JEFFAMINE D-230 (i.e., polyoxypropropylene diamine having an average molecular weight of 230 g/mole), JEFFAMINE D-400 (i.e., polyoxypropylene diamine having an average molecular weight of 400 g/mole), JEFFAMINE D-2000 (i.e., polyoxypropylene diamine having an average molecular weight of 2,000 g/mole), JEFFAMINE HK-511 (i.e., polyetherdiamine with both oxyethylene and oxypropylene groups and having an average molecular weight of 220 g/mole), JEFFAMINE ED-2003 (i.e., polypropylene oxide capped polyethylene glycol having an average molecular weight of 2,000 g/mole), and JEFFAMINE EDR-148 (i.e., triethyleneglycol diamine).

Exemplary alkylene diamines (i.e., G is a alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

Exemplary aralkylene diamines (i.e., G is an aralkylene such as alkylene-phenyl) include, but are not limited to 4-aminomethyl-phenylamine, 3-aminomethyl-phenylamine, and 2-aminomethyl-phenylamine. Exemplary alkylene-aralkylene diamines (i.e., G is an alkylene-aralkylene such as alkylene-phenylene-alkylene) include, but are not limited to, 4-aminomethyl-benzylamine, 3-aminomethyl-benzylamine, and 2-aminomethyl-benzylamine.

The following exemplary embodiments are provided by the present disclosure:

Embodiment 1

A compound of Formula I:

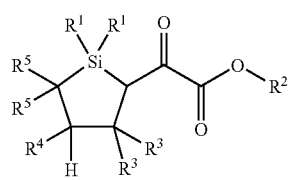

wherein: each $R^1$ is independently an alkyl, haloalkyl, aralkyl, alkenyl, aryl, or aryl substituted with an alkyl, alkoxy, or halo; $R^2$ is an alkyl, haloalkyl, aryl, or aryl substituted with an alkyl, alkoxy, halo, or alkoxycarbonyl; and each $R^3$, $R^4$, and $R^5$ is independently hydrogen or an alkyl, haloalkyl, aralkyl, alkenyl, aryl, or aryl substituted with an alkyl, alkoxy, or halo.

Embodiment 2

The compound of embodiment 1 wherein each $R^1$ is methyl.

Embodiment 3

The compound of embodiment 1 or 2 wherein $R^2$ is an alkyl having 1 to 4 carbon atoms or a haloalkyl having 1 to 4 carbon atoms, the alkyl or haloalkyl having a primary carbon atom or secondary carbon atom bonded to the adjacent oxy group.

Embodiment 4

The compound of any of embodiments 1 to 3 wherein $R^2$ is ethyl.

Embodiment 5

The compound of embodiment 1 or 2 wherein $R^2$ is a phenyl or a phenyl substituted with an alkyl having 1 to 4 carbon atoms, with an alkoxy having 1 to 4 carbon atoms, with a halo, or with an alkoxycarbonyl having 2 to 5 carbon atoms.

Embodiment 6

The compound of any of embodiments 1 to 5 wherein each $R^3$, $R^4$, and $R^5$ is hydrogen.

Embodiment 7

The compound of any of embodiments 1 to 5 wherein each $R^3$, $R^4$, and $R^5$ is an alkyl having 1 to 4 carbon atoms or a haloalkyl having 1 to 4 carbon atoms.

Embodiment 8

A method of making a polymer precursor of Formula III:

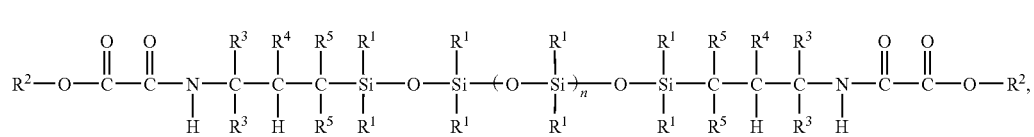

the method comprising combining under reaction conditions: a compound according to any of embodiments 1 to 7; and a silanol terminated siloxane of Formula II:

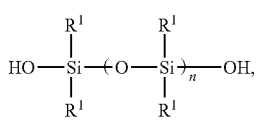

wherein: each $R^1$ is independently an alkyl, haloalkyl, aralkyl, alkenyl, aryl, or aryl substituted with an alkyl, alkoxy, or halo; and n is an integer of 0 to 1500.

Embodiment 9

The method of embodiment 8 wherein each $R^1$ is methyl.

Embodiment 10

A method of making a polymeric material comprising at least two repeat units of Formula VIII:

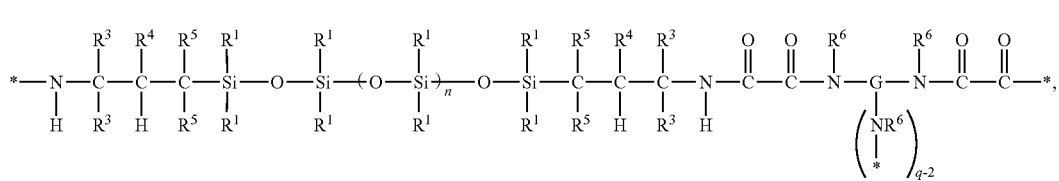

wherein q is an integer greater than or equal to 2, the method comprising combining under reaction conditions: a compound according to any of embodiments 1 to 7; and a silanol terminated siloxane of Formula II:

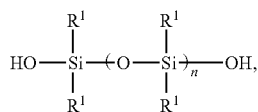

to form a polymer precursor of Formula III:

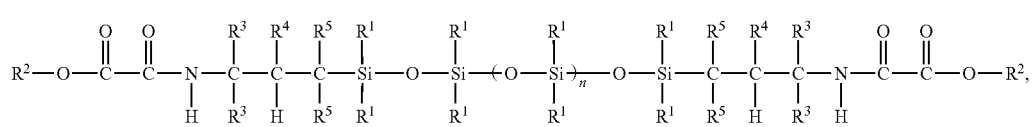

wherein: each $R^1$ is independently an alkyl, haloalkyl, aralkyl, alkenyl, aryl, or aryl substituted with an alkyl, alkoxy, or halo; $R^2$ is an alkyl, haloalkyl, aryl, or aryl substituted with an alkyl, alkoxy, halo, or alkoxycarbonyl; each $R^3$, $R^4$, and $R^5$ is independently hydrogen or an alkyl, haloalkyl, aralkyl, alkenyl, aryl, or aryl substituted with an alkyl, alkoxy, or halo; and n is an integer of 0 to 1500; and combining under reaction conditions the formed polymer precursor of Formula III with one or more amine compounds having on average a formula $G(NHR^6)_r$; wherein: G is a residue unit equal to the formula $G(NHR^6)_r$ minus the r —$NHR^6$ groups; $R^6$ is hydrogen or alkyl or $R^6$ taken together with G and with the nitrogen to which they are both attached forms a heterocyclic group; and r is a number greater than or equal to 2.

Embodiment 11

The method of embodiment 10 wherein each $R^1$ is methyl.

Embodiment 12

A method of making a compound of Formula I, the method comprising: subjecting a compound of Formula VII to conditions effective to cause cyclization:

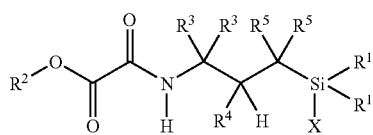

wherein: each $R^1$ is independently an alkyl, haloalkyl, aralkyl, alkenyl, aryl, or aryl substituted with an alkyl, alkoxy, or halo; $R^2$ is an alkyl, haloalkyl, aryl, or aryl substituted with an alkyl, alkoxy, halo, or alkoxycarbonyl; each $R^3$, $R^4$, and $R^5$ is independently hydrogen or an alkyl, haloalkyl, aralkyl, alkenyl, aryl, or aryl substituted with an alkyl, alkoxy, or halo; and X is a halogen.

Embodiment 13

The method of embodiment 12 wherein conditions effective to cause cyclization comprise providing an organic base.

Embodiment 14

The method of embodiment 13 wherein the organic base is provided in a solvent.

Embodiment 15

The method of embodiment 13 or 14 wherein the organic base is triethylamine.

Embodiment 16

The method of any of embodiments 12 to 15 wherein each $R^1$ is methyl.

Embodiment 17

The method of any of embodiments 12 to 16 wherein $R^2$ is an alkyl having 1 to 4 carbon atoms or a haloalkyl having 1 to 4 carbon atoms, the alkyl or haloalkyl having a primary carbon atom or secondary carbon atom bonded to the adjacent oxy group.

Embodiment 18

The method of any of embodiments 12 to 17 wherein $R^2$ is ethyl.

Embodiment 19

The method of any of embodiments 12 to 16 wherein $R^2$ is a phenyl or a phenyl substituted with an alkyl having 1 to 4 carbon atoms, with an alkoxy having 1 to 4 carbon atoms, with a halo, or with an alkoxycarbonyl having 2 to 5 carbon atoms.

Embodiment 20

The method of any of embodiments 12 to 19 wherein each $R^3$, $R^4$, and $R^5$ is hydrogen.

Embodiment 21

The method of any of embodiments 12 to 19 wherein each $R^3$, $R^4$, and $R^5$ is an alkyl having 1 to 4 carbon atoms or a haloalkyl having 1 to 4 carbon atoms.

Embodiment 22

The method of any of embodiments 12 to 21 wherein X is Cl.

The foregoing describes the invention in terms of embodiments foreseen by the inventors for which an enabling description was available, notwithstanding that insubstantial modifications of the invention, not presently foreseen, may nonetheless represent equivalents thereto.

EXAMPLES

These examples are merely for illustrative purposes only and are not meant to be limiting on the scope of the appended claims. All parts, percentages, ratios, and the like in the examples are by weight, unless noted otherwise. Solvents and other reagents used were obtained from Sigma-Aldrich Chemical Company; Milwaukee, Wis. unless otherwise noted.

Preparative Example 1

N-Allylamido Ethyl Oxalate

Diethyl oxalate (256.00 grams) was charged to a round bottom flask and cooled to 0-5° C., and 50 g allylamine was added slowly to the stirred solution. The reaction was allowed to warm to ambient temperature. After mixing overnight, ethanol and the excess diethyl oxalate were removed under reduced pressure. The residue was distilled in vacuo and the product collected as a clear, colorless liquid (boiling point 72-76° C., 1 Torr), and the yield was 111 grams.

Preparative Example 2

3-(Chlorodimethylsilyl propylamido) ethyl oxalate

A glass pressure vessel was charged with 22.58 g of chlorodimethylsilane, 30.00 g of N-allylamido ethyl oxalate as prepared in Preparative Example 1, and 4 drops of a 2.3% solution of bis(divinyltetramethyldisiloxane)platinum complex (i.e., Pt hydrosilation catalyst. The vessel was sealed and heated to 70-80° C. for 16 hours. The clear, yellow liquid was cooled to ambient temperature, the residual pressure slowly released, and the contents reheated with stirring to 80° C. to remove excess chlorodimethylsilane. Gas chromatographic analysis revealed the presence of only approximately 5% unreacted N-allylamido ethyl oxalate starting material, and the yield was 49 grams.

Example 1

N-Ethyl Oxalyl Aza Sila Cyclopentane

Formula I with $R^1=R^2=R^3=H$

The crude product from Preparative Example 2 was dissolved in 110 g of toluene. Triethylamine, 21.10 g, was added dropwise with stirring, and a copious precipitate immediately formed. After 16 hours, the mixture was filtered through a fritted glass funnel under nitrogen pressure, the filter cake washed with additional toluene, and the solvent removed on a rotary evaporator under reduced pressure. The residue was distilled in vacuo, and the cyclic silazane isolated as a clear, colorless liquid (boiling point 84° C., 1 Torr). The yield was 32.55 g (89%). NMR analysis confirmed the structure as the cyclic silazane indicated in Formula I with $R^1=R^2=R^3=H$.

Example 2

Conversion of a Silanol Terminated Silicone into N-Ethyl Oxalamidopropyl Terminated Silicone A 4200 MW silanol terminated silicone fluid (71.68 g) was heated under vacuum at 100° C. for 10 minutes and then cooled to ambient temperature under nitrogen. A cyclic silazane of Formula I with $R^1=R^2=R^3=H$ and as prepared in Example 1 (3.86 grams) was added and the contents stirred at 50° C. for 0.5 hour. Gas chromatographic analysis showed the complete disappearance of the cyclic silazane. An additional 3.86 grams of cyclic silazane of Formula I with $R^1=R^2=R^3=H$ was added, and heating continued until the silazane was no longer consumed. The product was heated under vacuum at 150° C. (1 Torr) to completely remove any unreacted cyclic silazane and then cooled to ambient temperature. NMR analysis revealed that 100% of the silanol chain ends had been converted into the ethyl oxalyl amidopropyl chain ends.

Example 3

Preparation of a Silicone Polyoxamide

N-Ethyl oxalamidopropyl terminated silicone as prepared in Example 2 (10.0 grams) was charged to a 4 ounce wide mouth jar with rapid stirring, and ethylene diamine (0.13 gram) was quickly added. After approximately 30 seconds, the reaction had solidified to a frothy solid. After 24 hours, the product was dissolved in 40 ml of THF over another 24 hour period. The viscous solution was cast into a glass Petri dish and the solvent allowed to evaporate to dryness to provide a clear, very strong elastomeric film of the silicone polyoxamide.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A method of making a polymer precursor of Formula III:

$$R^2-O-\overset{O}{\overset{\|}{C}}-\overset{O}{\overset{\|}{C}}-\underset{H}{N}-\overset{R^3}{\underset{R^3}{C}}-\overset{R^4}{\underset{H}{C}}-\overset{R^5}{\underset{R^5}{C}}-\overset{R^1}{\underset{R^1}{Si}}-O-\overset{R^1}{\underset{R^1}{Si}}(-O-$$

-continued $$-\overset{R^1}{\underset{R^1}{Si}})_n-O-\overset{R^1}{\underset{R^1}{Si}}-\overset{R^5}{\underset{R^5}{C}}-\overset{R^4}{\underset{H}{C}}-\overset{R^3}{\underset{R^3}{C}}-\underset{H}{N}-\overset{O}{\overset{\|}{C}}-\overset{O}{\overset{\|}{C}}-O-R^2,$$

the method comprising combining under reaction conditions:

a compound of Formula I:

wherein:
- each $R^1$ is independently an alkyl, haloalkyl, aralkyl, alkenyl, aryl, or aryl substituted with an alkyl, alkoxy, or halo;
- $R^2$ is an alkyl, haloalkyl, aryl, or aryl substituted with an alkyl, alkoxy, halo, or alkoxycarbonyl; and
- each $R^3$, $R^4$, and $R^5$ is independently hydrogen or an alkyl, haloalkyl, aralkyl, alkenyl, aryl, or aryl substituted with an alkyl, alkoxy, or halo; and a silanol terminated siloxane of Formula II:

$$HO-\overset{R^1}{\underset{R^1}{Si}}(-O-\overset{R^1}{\underset{R^1}{Si}})_n-OH,$$

wherein:
- each $R^1$ is independently an alkyl, haloalkyl, aralkyl, alkenyl, aryl, or aryl substituted with an alkyl, alkoxy, or halo; and
- n is an integer of 0 to 1500.

2. The method of claim 1 wherein each $R^1$ is methyl.

3. A method of making a polymeric material comprising at least two repeat units of Formula VIII:

$$*-\underset{H}{N}-\overset{R^3}{\underset{R^3}{C}}-\overset{R^4}{\underset{H}{C}}-\overset{R^5}{\underset{R^5}{C}}-\overset{R^1}{\underset{R^1}{Si}}-O-\overset{R^1}{\underset{R^1}{Si}}(-O-\overset{R^1}{\underset{R^1}{Si}})_n-O-\overset{R^1}{\underset{R^1}{Si}}-\overset{R^5}{\underset{R^5}{C}}-\overset{R^4}{\underset{H}{C}}-\overset{R^3}{\underset{R^3}{C}}-\underset{H}{N}-\overset{O}{\overset{\|}{C}}-\overset{O}{\overset{\|}{C}}-\underset{R^6}{N}-G\underset{\left(\underset{*}{NR^6}\right)_{q-2}}{-}\underset{R^6}{N}-\overset{O}{\overset{\|}{C}}-\overset{O}{\overset{\|}{C}}-*,$$

wherein q is an integer greater than or equal to 2, the method comprising combining under reaction conditions:

a compound of Formula I:

wherein:
- each $R^1$ is independently an alkyl, haloalkyl, aralkyl, alkenyl, aryl, or aryl substituted with an alkyl, alkoxy, or halo;
- $R^2$ is an alkyl, haloalkyl, aryl, or aryl substituted with an alkyl, alkoxy, halo, or alkoxycarbonyl; and
- each $R^3$, $R^4$, and $R^5$ is independently hydrogen or an alkyl, haloalkyl, aralkyl, alkenyl, aryl, or aryl substituted with an alkyl, alkoxy, or halo; and a silanol terminated siloxane of Formula II:

$$HO-\overset{R^1}{\underset{R^1}{Si}}(-O-\overset{R^1}{\underset{R^1}{Si}})_n-OH,$$

to form a polymer precursor of Formula III:

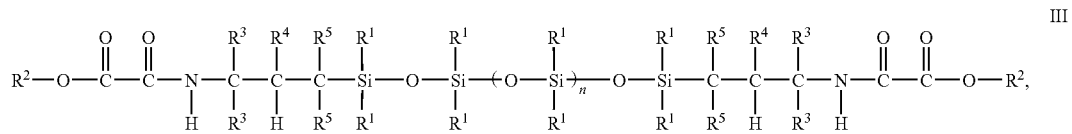

wherein:
- each $R^1$ is independently an alkyl, haloalkyl, aralkyl, alkenyl, aryl, or aryl substituted with an alkyl, alkoxy, or halo;
- $R^2$ is an alkyl, haloalkyl, aryl, or aryl substituted with an alkyl, alkoxy, halo, or alkoxycarbonyl;
- each $R^3$, $R^4$, and $R^5$ is independently hydrogen or an alkyl, haloalkyl, aralkyl, alkenyl, aryl, or aryl substituted with an alkyl, alkoxy, or halo; and
- n is an integer of 0 to 1500; and combining under reaction conditions the formed polymer precursor of Formula III with one or more amine compounds having on average a formula $G(NHR^6)_r$;

wherein:
- G is a residue unit equal to the formula $G(NHR^6)_r$ minus the r —$NHR^6$ groups;
- $R^6$ is hydrogen or alkyl or $R^6$ taken together with G and with the nitrogen to which they are both attached forms a heterocyclic group; and
- r is a number greater than or equal to 2.

4. The method of claim 3 wherein each $R^1$ is methyl.

5. A method of making a compound of Formula I, the method comprising:

subjecting a compound of Formula VII to conditions effective to cause cyclization:

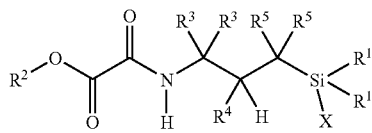

wherein:
- each $R^1$ is independently an alkyl, haloalkyl, aralkyl, alkenyl, aryl, or aryl substituted with an alkyl, alkoxy, or halo;
- $R^2$ is an alkyl, haloalkyl, aryl, or aryl substituted with an alkyl, alkoxy, halo, or alkoxycarbonyl;
- each $R^3$, $R^4$, and $R^5$ is independently hydrogen or an alkyl, haloalkyl, aralkyl, alkenyl, aryl, or aryl substituted with an alkyl, alkoxy, or halo; and
- X is a halogen.

6. The method of claim 5 wherein conditions effective to cause cyclization comprise providing an organic base.

7. The method of claim 6 wherein the organic base is provided in a solvent.

8. The method of claim 6 wherein the organic base is triethylamine.

9. The method of claim 5 wherein each $R^1$ is methyl.

10. The method of claim 5 wherein $R^2$ is an alkyl having 1 to 4 carbon atoms or a haloalkyl having 1 to 4 carbon atoms, the alkyl or haloalkyl having a primary carbon atom or secondary carbon atom bonded to the adjacent oxy group.

11. The method of claim 10 wherein $R^2$ is ethyl.

12. The method of claim 5 wherein $R^2$ is a phenyl or a phenyl substituted with an alkyl having 1 to 4 carbon atoms, with an alkoxy having 1 to 4 carbon atoms, with a halo, or with an alkoxycarbonyl having 2 to 5 carbon atoms.

13. The method of claim 5 wherein each $R^3$, $R^4$, and $R^5$ is hydrogen.

14. The method of claim 5 wherein each $R^3$, $R^4$, and $R^5$ is an alkyl having 1 to 4 carbon atoms or a haloalkyl having 1 to 4 carbon atoms.

15. The method of claim 5 wherein X is Cl.

\* \* \* \* \*

UNITED STATES PATENT AND TRADEMARK OFFICE
CERTIFICATE OF CORRECTION

| | |
|---|---|
| PATENT NO. | : 7,652,163 B2 |
| APPLICATION NO. | : 12/368757 |
| DATED | : January 26, 2010 |
| INVENTOR(S) | : Charles M Leir |

It is certified that error appears in the above-identified patent and that said Letters Patent is hereby corrected as shown below:

Column 3

Line 61; Delete "body care" and insert -- bodycare --, therefor.

Column 5

Line 12; Delete "—$R^3$—Ar" and insert -- —$R^a$—Ar --, therefor.
Line 15; Delete "Ara" and insert -- $Ar^a$ --, therefor.

Column 6

Line 22; Delete "thereof," and insert -- thereof; --, therefor.
Line 58; After "with" insert -- Attorney Docket Nos. 63217US002 --.
Line 60; Before "Ser. No." insert -- 63219US002 --.
Line 62; Before "Ser. No." insert -- 63284US002 --.
Line 65; Before "Ser. No." insert -- 63311US002 --.

Column 9

Line 6-7; Delete "divinyltetramethyldisoloxane" and insert
-- divinyltetramethyldisiloxane --, therefor.

Column 10

Line 33; Delete "2, %," and insert -- 2%, --, therefor.

Signed and Sealed this
First Day of May, 2012

David J. Kappos
*Director of the United States Patent and Trademark Office*

CERTIFICATE OF CORRECTION (continued)

Column 11-12

1st structure; Delete " 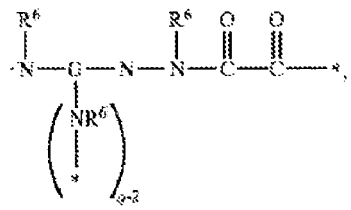 " and insert

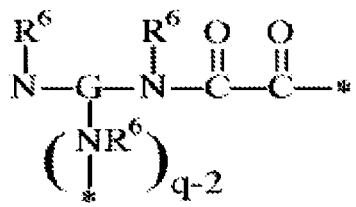

-- --, therefor.

Column 11

Line 38; Delete "G(NHR$^6$)," and insert -- G(NHR$^6$)$_r$, -- therefor.
Line 67; Delete "diethylentriamine," and insert -- diethylenetriamine, --, therefor.

Column 12

Line 3; Delete "polyoxypropropylene" and insert -- polyoxypropylene --, therefor.
Line 5; Delete "polyoxypropropylene" and insert -- polyoxypropylene --, therefor.

Column 12

Line 40; Delete "polyoxypropropylene" and insert -- polyoxypropylene --, therefor.

Column 13

Line 20 (Structure); Delete " 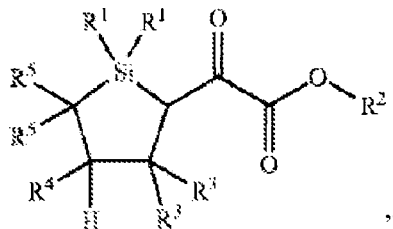 " and insert

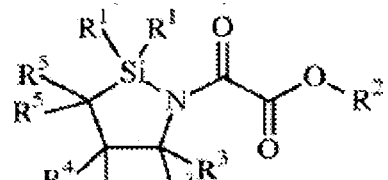

-- --, therefor.

CERTIFICATE OF CORRECTION (continued)
U.S. Pat. No. 7,652,163 B2

Column 18

Line 2; Delete "divinyltetramethyldisoloxane" and insert
-- divinyltetramethyldisiloxane --, therefor.